US012718091B2

(12) United States Patent
Tang

(10) Patent No.: US 12,718,091 B2
(45) Date of Patent: Aug. 25, 2026

(54) LARGE KERNEL CONVOLUTIONAL NEURAL NETWORK

(71) Applicant: THE MITRE CORPORATION, McLean, VA (US)

(72) Inventor: Huang Tang, McLean, VA (US)

(73) Assignee: The MITRE Corporation, McLean, VA (US)

( * ) Notice: Subject to any disclaimer, the term of this patent is extended or adjusted under 35 U.S.C. 154(b) by 836 days.

(21) Appl. No.: 17/947,637

(22) Filed: Sep. 19, 2022

(65) Prior Publication Data

US 2023/0153605 A1 May 18, 2023

Related U.S. Application Data

(60) Provisional application No. 63/279,853, filed on Nov. 16, 2021.

(51) Int. Cl.
*G06N 3/08* (2023.01)
*G16H 50/70* (2018.01)

(52) U.S. Cl.
CPC ............... *G06N 3/08* (2013.01); *G16H 50/70* (2018.01)

(58) Field of Classification Search
CPC ........................................................ G06N 3/08
See application file for complete search history.

(56) References Cited

U.S. PATENT DOCUMENTS

| | | | |
|---|---|---|---|
| 9,135,553 | B2 | 9/2015 | Kato et al. |
| 2008/0015891 | A1 | 1/2008 | Lee |
| 2018/0247195 | A1 | 8/2018 | Kumar et al. |
| 2020/0356846 | A1 | 11/2020 | Saripalli et al. |

FOREIGN PATENT DOCUMENTS

| | | |
|---|---|---|
| CN | 107863147 A | 3/2018 |

OTHER PUBLICATIONS

Suo, Qiuling, Fenglong Ma, Ye Yuan, Mengdi Huai, Weida Zhong, Aidong Zhang, and Jing Gao. "Personalized disease prediction using a CNN-based similarity learning method." In 2017 IEEE International Conference on Bioinformatics and Biomedicine (BIBM), pp. 811-816. IEEE, 2017. (Year: 2017).*

(Continued)

*Primary Examiner* — Kakali Chaki
*Assistant Examiner* — Charles Jeffrey Jones
(74) *Attorney, Agent, or Firm* — Sterne, Kessler, Goldstein & Fox P.L.L.C.

(57) ABSTRACT

Disclosed herein are system, method, and computer program product embodiments for generating a disease severity index based on a machine learning system executing a one-dimensional convolutional neural network (CNN) using a large kernel. An embodiment operates by collecting training data sets, extracting a training data feature set from the training data sets, weighting features in the training data feature set to generate a weighted training data feature set, selecting a large kernel comprising the weighted training data feature set, executing a one-dimensional convolution of the weighted training data feature set based on the large kernel to generate an aggregation of weighted occurrences and generating an index based on the aggregation of weighted occurrences.

19 Claims, 6 Drawing Sheets

ONE-DIMENSIONAL CNN
300

(56) References Cited

OTHER PUBLICATIONS

Rajpurkar, Pranav, Awni Y. Hannun, Masoumeh Haghpanahi, Codie Bourn, and Andrew Y. Ng. "Cardiologist-level arrhythmia detection with convolutional neural networks." arXiv preprint arXiv:1707.01836 (2017). (Year: 2017).*
West, David, and Scott Dellana. "An empirical analysis of neural network memory structures for basin water quality forecasting." International Journal of Forecasting 27 (2011): 777-803. (Year: 2011).*
Carrington, A., Kernel Methods and Measures for Classification with Transparency, Interpretability and Accuracy in Health Care, University of Waterloo, 2018.
Xiao et al., "Opportunities and challenges in developing deep learning models using electronic health records data: a systematic review" Journal of the American Medical Informatics Association, 25(10), 2018, 1419-1428.
Mikalsen et al., A Kernel to Exploit Informative Missingness in Multivariate Time Series from EHRs, The Arctic University of Norway, Feb. 2020.

* cited by examiner

LARGE KERNEL CONVOLUTIONAL NEURAL NETWORK

STATEMENT REGARDING FEDERALLY-SPONSORED RESEARCH AND DEVELOPMENT

The U.S. government has a paid-up license in this invention and the right in limited circumstances to require the patent owner to license others on reasonable terms as provided for by the terms of Contract No. TIRN099D0005 awarded by the DoD Joint Artificial Intelligence Center; Defense Health Agency.

BACKGROUND

When analyzing a time series of medical events, a common practice is to create bins of encounter counters. However, this method is not tunable for different evolving characteristics of various health conditions as severity and recency may not be properly weighted or distinguished.

BRIEF DESCRIPTION OF THE DRAWINGS

The accompanying drawings are incorporated herein and form a part of the specification.

In the drawings, like reference numbers generally indicate identical or similar elements. Additionally, generally, the left-most digit(s) of a reference number identifies the drawing in which the reference number first appears.

DETAILED DESCRIPTION

Provided herein are system, apparatus, device, method and/or computer program product embodiments, and/or combinations and sub-combinations thereof, for Machine-Learning (ML) technology for discrete and irregular time series analysis. In machine-learning longitudinal analysis, there are two types of time series. On one end of the spectrum, there is continuous observation over a considerable time window. On the other end, observations are scattered and irregular.

In some embodiments, the technology described herein analyzes time series of the latter type. Binned methods cannot properly deal with a diminishing impact of a same type event if it happened a long time ago instead of most recently. For example, if one goal were to identify a severity of a medical diagnosis, an illness 5 years ago would carry less weight than a recent occurrence. Interactions between different time-series is mostly unknown. Therefore, in some embodiments, the technology described herein implements a one-dimensional Convolutional Neural Network (CNN). Contrast this with Multi-dimensional CNN that implicitly depends on comorbidity interactions, which is usually unknown a priori and therefore may not be an optimum filter (kernel) build. For example, a CNN with symmetric kernels over a small stride is not effective in capturing the evolution of chronical diseases, which evolve over several years. More specifically, it fails to consider the kernel variation to capture different decaying property and casual structures.

The technology described herein implements large kernels based on Gamma distributions. This method effectively resolves both drawbacks of the pre-mentioned methods and largely increases the efficiency and performance of the predictive models.

Figure 1:
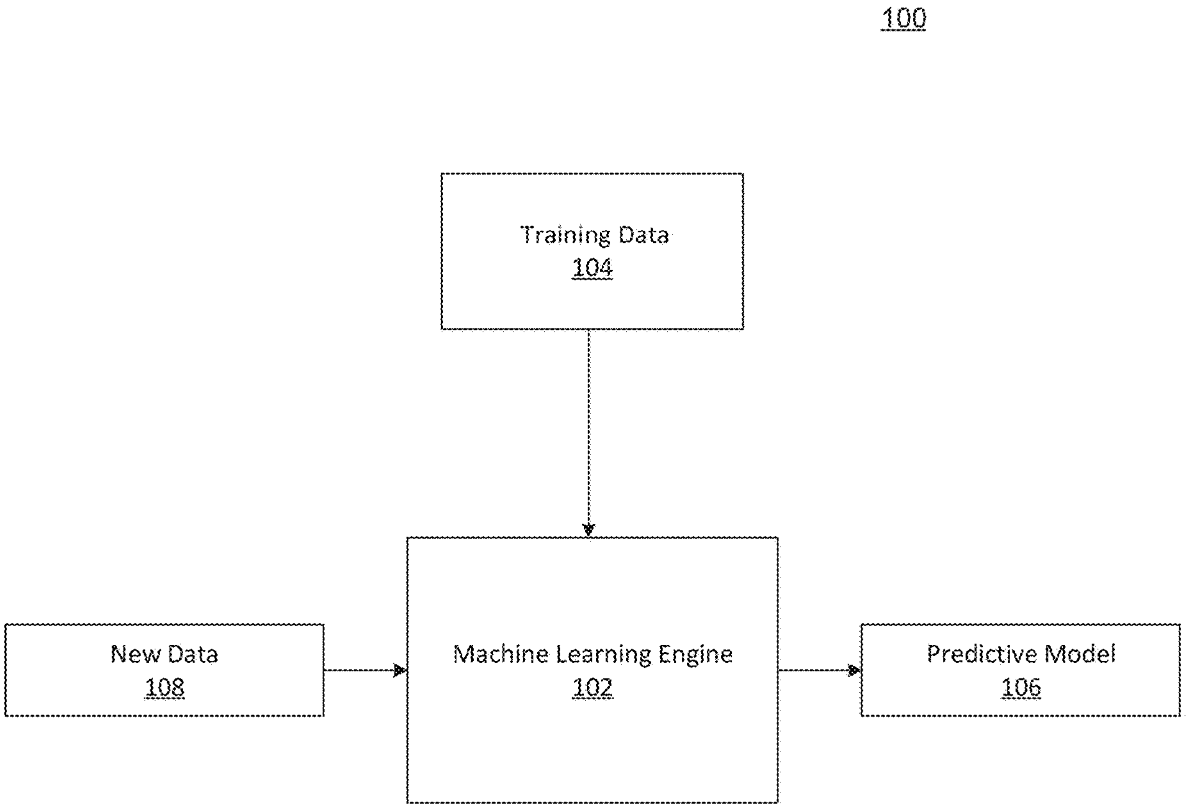
FIG. 1 is a block diagram of a machine-learning system, according to some embodiments.

FIG. 1 illustrates a machine learning system, according to some embodiments. In machine learning, a common task is the study and construction of algorithms that can learn from and make predictions on data. Such algorithms function by making data-driven predictions or decisions, through building a mathematical model from input data. Machine learning involves computers discovering how they can perform tasks without being explicitly programmed to do so. It involves a machine-learning engine 102 learning from an input training data set 104 that performs certain tasks.

A predictive model 106 uses statistics to predict outcomes. Most often, the event one wants to predict is in the future, but predictive modeling can be applied to any type of unknown event, regardless of when it occurred. In many cases, the model is chosen on the basis of detection theory to try to guess the probability of an outcome given a set amount of input data, for example, given an email, attempting to predict how likely that it is spam. Models can use one or more classifiers in trying to determine the probability of a set of data belonging to another set.

Machine learning approaches are traditionally divided into three broad categories, depending on the nature of the "signal" or "feedback" available to the learning system. In a first category, supervised learning, the machine-learning engine 102 is presented with training data 104 including example inputs and their desired outputs, given by a "teacher", and the goal is to learn a general rule that maps inputs to outputs. In a second category, unsupervised learning, no labels are given to the learning algorithm, leaving the ML system on its own to find structure in its input. Unsupervised learning can be a goal in itself (discovering hidden patterns in data) or a means towards an end (feature learning). In a third category, reinforcement learning, a computer program interacts with a dynamic environment in which it must perform a certain goal (such as driving a vehicle or playing a game against an opponent). As it navigates its problem space, the program is provided feedback analogous to rewards, which it tries to maximize.

A model is initially fit to a training data set 104, which is a set of examples used to fit the parameters (e.g., weights of connections between neurons in artificial neural networks) of the model. The model (e.g., a neural net or a naive Bayes classifier) is trained on the training dataset using a supervised learning method, for example using optimization methods such as gradient descent or stochastic gradient descent. In practice, the training dataset often consists of pairs of an input vector (or scalar) and the corresponding output vector (or scalar), where the answer key is commonly denoted as the target (or label). The current model is executed with the training dataset and produces a result, which is then compared with the target, for each input vector in the training dataset. Based on the result of the comparison and the specific learning algorithm being used, the parameters of the model are adjusted (tuned).

Successively, the fitted model is used to predict the responses for the observations in a second dataset called the validation dataset (development dataset). The validation dataset provides an unbiased evaluation of a model fit on the training dataset while tuning the model's hyper-parameters (e.g., the number of hidden units—layers and layer widths—in a neural network).

Finally, the test dataset is a new dataset 108 used to provide an unbiased evaluation of a final predictive model 106 fit on the training dataset. The testing set should follow the same probability distribution as the training dataset.

Figure 2:
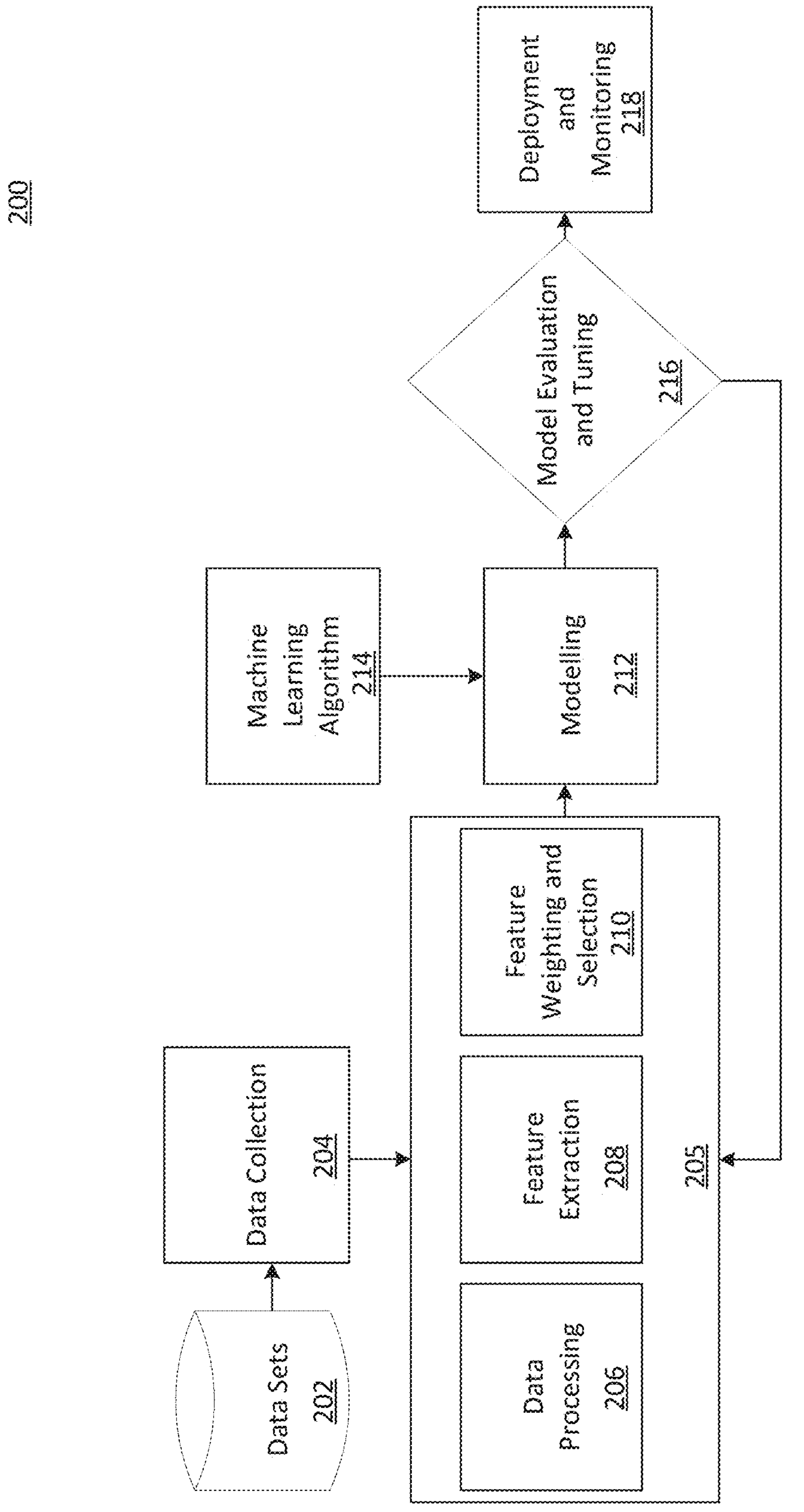
FIG. 2 is a flowchart illustrating a modeling process, according to some embodiments.

FIG. 2 illustrates a block diagram of a process flow for a machine learning system, according to some embodiments.

Data is collected in a data collection stage 204. Data collection of datasets 202 is improved by capturing an end user's requirements, determining the data needs to be collected, and determining how any given data is going to contribute to the predictive model. Based on the data collection results, data sources may be allocated, and data sets can subsequently be acquired from different sources. For example, electronic medical records may be used to train the machine learning system to predict disease or reflect injury severity levels over time.

Data processing/preparation stage 205 ingests data sets 202 from data collection stage 204. During the data processing/preparation stage 205, raw data will first be extracted, transformed, and loaded into a data store (e.g., database (DB), not shown). This stage includes processing to clean up the data—for example, removing empty/null values, detecting outliers, and converting data types. Data processing 206 is performed in conjunction with exploratory data analysis (EDA) to appropriately understand the data, discover relationships and correlations between data, and determine which features may be useful (feature extraction 208). Useful features are those that have predictive capability (produce high correlation) in a predictive model. Data preprocessing, wrangling, and feature engineering may be implemented in the Data processing/preparation stage 205 using, for example, Structured Query Language (SQL) queries.

However, not all data fields are directly suitable for machine learning model inputs, which require proper encoding. In stage 210, features are selected and weighted (higher/lower value relative to other selected features). For example, not all values may be in the correct numerical scale and not all data shall bear the same weights as model inputs.

Modelling stage 212 may include building a machine-learning model using the processed data as training data to machine learning algorithm 214. For example, a model is built that can evaluate for different evolving characteristics of various health conditions. In some embodiments, a health severity index may be generated based on selection of thresholds of severity (See FIG. 4). This is a supervised learning approach involving logistic regression and random forest methods.

Model evaluation and tuning stage 216 provides evaluation of the machine model after training where the machine learning model is evaluated by several metrics/scores and tuned for performance (if applicable). For classification models, metrics can include accuracy, precision, recall, and area under a receiver operating characteristics (ROC) curve. If the model performance is insufficient, processing may be redirected to the fine tuning stage to reevaluate and further clean data, select new features for the model, or obtain additional data. In another example embodiment, model performance is improved by adjusting model hyper-parameters. In machine learning, a hyper-parameter is a parameter whose value is used to control the learning process. By contrast, the values of other parameters (typically node weights) are derived via training.

Model deployment and monitoring stage 218 includes deploying the trained and tuned machine-learning model in production and monitoring to ensure that the model is correctly predicting its target variable. If the model performance decreases, then the model can be retuned or rebuilt, followed by a subsequent model evaluation.

Figure 3:
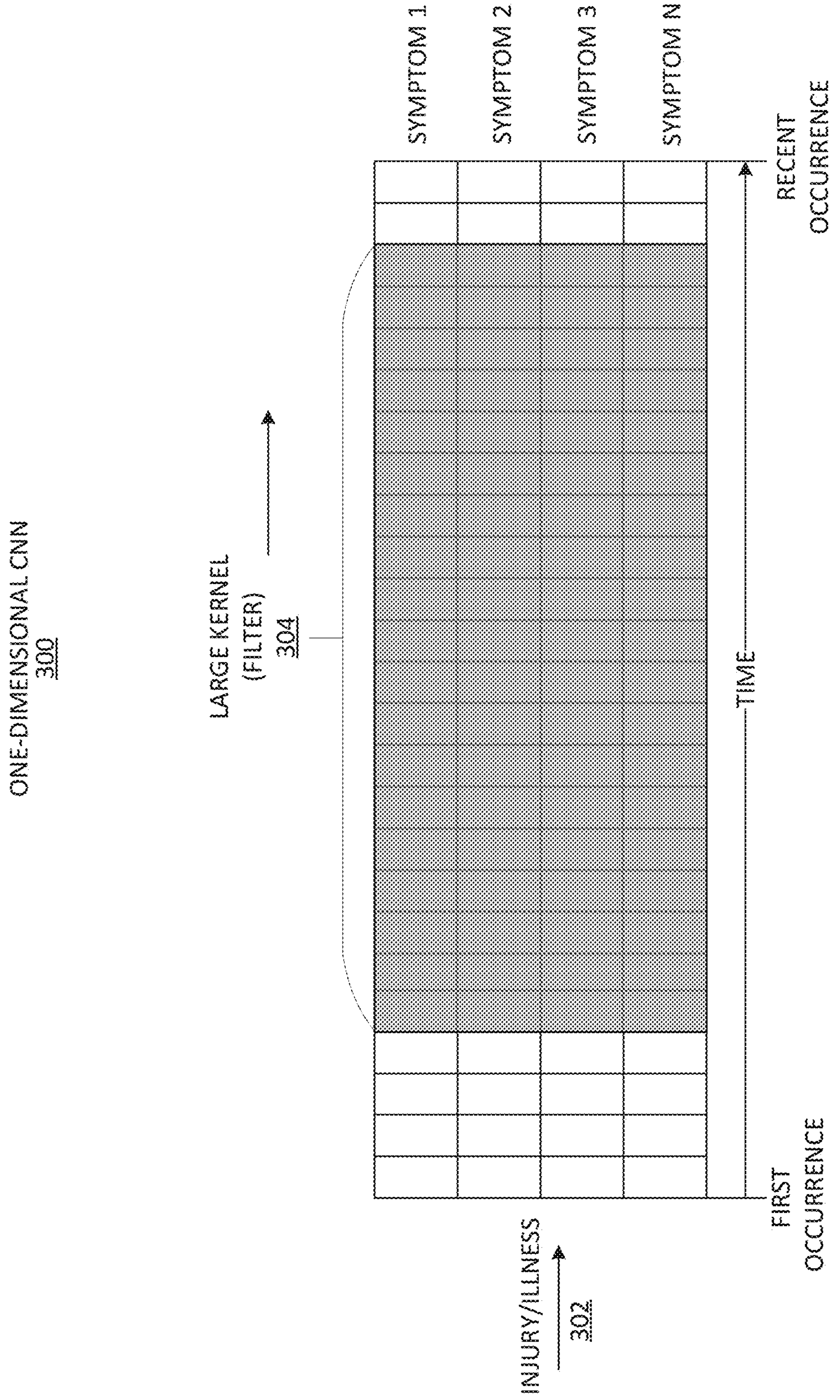
FIG. 3 is an example one-dimensional large kernel CNN, according to some embodiments.

FIG. 3 illustrates a one-dimensional (1D) convolutional neural network (CNN), according to some embodiments.

CNN architecture is conventionally formed by a stack of distinct layers (filters) that transform the input volume into an output volume (e.g., holding the class scores) through a differentiable function. A few distinct types of layers are commonly used. The convolutional layer is the core building block of a CNN. The layer's parameters consist of a set of learnable filters (or kernels), which have a small receptive field.

For a single layer 1-dimensional CNN, during a forward pass of a large kernel (filter), each filter is convolved across the height of the input volume, computing the dot product between the filter entries and the input, producing a 1-dimensional activation map of that filter. As a result, the network learns filters that activate when it detects some specific type of feature at some spatial position in the input.

The filters include vector of weights and bias and represent particular features of the input (e.g., a particular shape). A distinguishing feature of CNNs is that many neurons can share the same filter. This reduces the memory footprint because a single bias and a single vector of weights may be used across all receptive fields that share that filter, as opposed to each receptive field having its own bias and vector weighting.

As shown in FIG. 3, a one-dimensional (1D) convolutional neural network (CNN) 300 preprocesses temporal relations between encounters (injury/illness) related to any given medical condition. A one-dimensional CNN has no depth, only height and length. As shown, height is illustrated as a series of potential symptoms (1-N). While shown as symptoms (conditions), the height could be any time series feature without departing from the scope of the technology described herein. For example, each of the height segmentations may be medical codes, known diseases, injuries or non-medical features. In this example embodiment, the length of the one-dimensional CNN is time. For example, a series of medical conditions is tracked in a time series from first occurrence of the injury/illness to the most recent occurrence.

As interactions between different occurrences in the time-series is mostly unknown, a large kernel (covering a plurality of occurrences over an extended time-period) is implemented. A CNN with symmetric kernels over a small stride is not effective in capturing the evolution of chronical diseases, which evolve over several years. More specifically, it fails to consider the kernel variation to capture different decaying property and casual structures.

A large kernel (filter) 304 as it moves across the data (forward pass) from left to right (oldest to newest occurrence) processes the data within the kernel and captures spatially related data (e.g., temporal relations between encounters (injury/illness) related to any given medical condition.) In addition, weighting of the large kernel is increased over time, with most recent occurrences given a highest weighting and oldest occurrences given a lowest weighting. While shown as a specific size and position, the large kernel may be of any size that captures a plurality of occurrences of the feature set being analyzed over time (time series).

In some embodiments, an application of a large kernel gamma window function may be used to process the data. The gamma function behaves like a factorial for natural numbers (a discrete set). However, its extension to the positive real numbers (a continuous set) makes it useful for modeling situations involving continuous change, with applications to calculus, differential equations, complex analysis, and statistics. The gamma distribution function provides a parametric family of probability asymmetric distributions with a long tail. A long tail of some distributions of numbers is the portion of the distribution having many occurrences far from the "head" or central part of the distribution.

Figure 4:
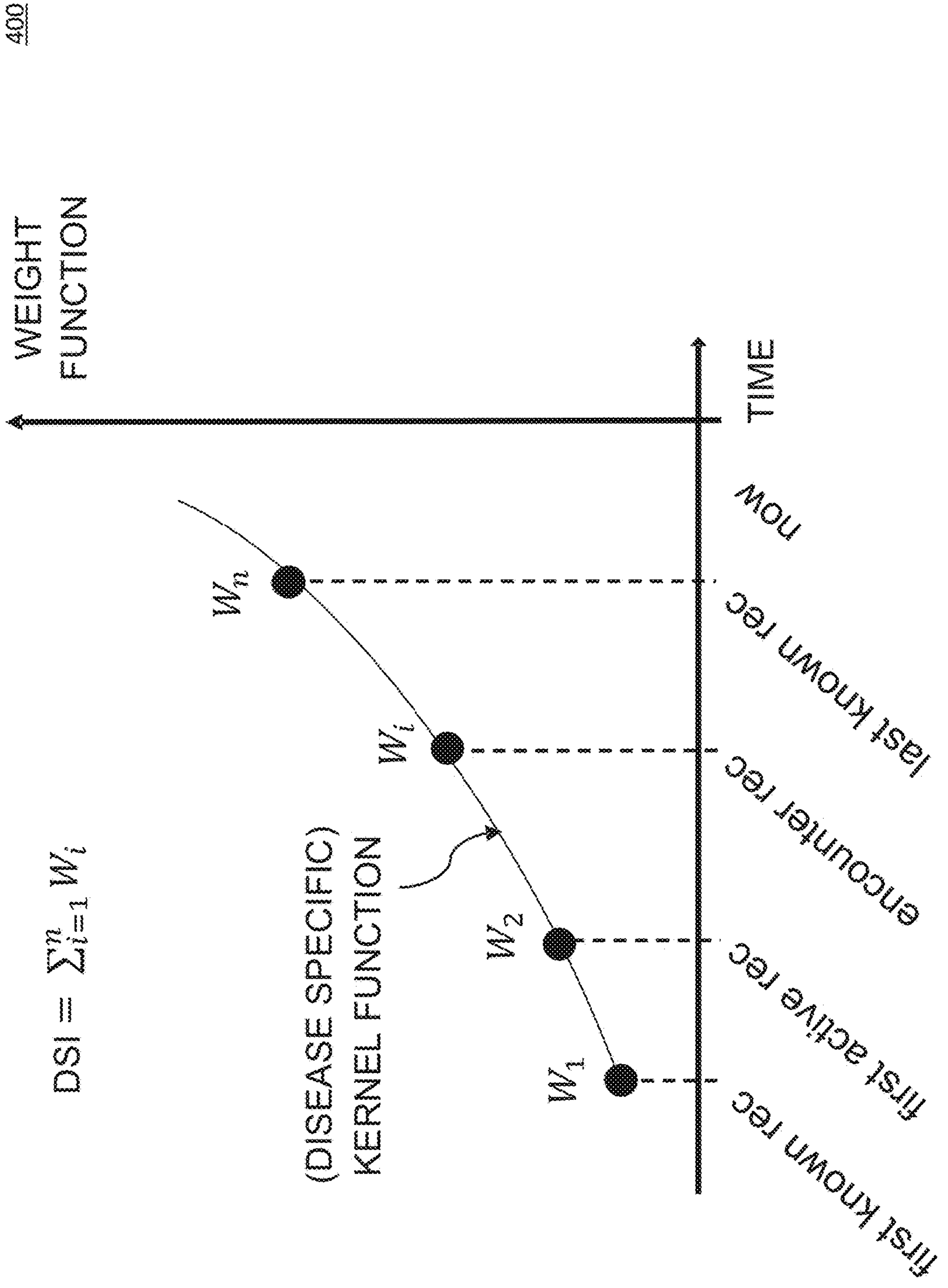
FIG. 4 is an example graph illustrating a weighted large kernel function, according to some embodiments.

A gamma window function applied to the data creates a weighted historical average (See FIG. 4). The function weights recent medical data more than older medical history. This allows for summarizing the monotonic progression of a health deterioration process per medical condition code as a single predictor.

FIG. 4 is an example graph illustrating a weighted large kernel function, according to some embodiments. Method 400 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIG. 4, as will be understood by a person of ordinary skill in the art.

In some embodiments, method 400, the disease model is implemented according to time-dependent medical encounter data aggregated into a disease severity index. The disease severity index (DSI) is an aggregation of the weighted occurrences as per:

$$DSI=\Sigma^{n}_{i-1}W_i$$

As shown, recorded occurrences of an injury/disease are assigned increasing weights over time. For example, a first known recorded occurrence is weighted with a low importance. A first active recorded occurrence is weighted as a higher importance. An encounter recorded occurrence is assigned a higher weighted importance. Lastly, the last known occurrence recorded is given the highest weight.

The models (logistic regression and random forest) were trained on a controlled training data set with hyper-parameters chosen by cross-validation. The trained model may predict injury/disease/disability severity indexes based on electronic health records (EHRs) and patient records using the machine learning technologies as described in association with FIGS. 1-3.

In some embodiments, the predictive models and techniques successfully tested on a top X frequent conditions may be extended to other conditions, provided that the condition is not extremely rare (less than 500 recorded cases in the past 20 years). In addition, predictive models may be focused on specific conditions individually or holistically.

Figure 5:
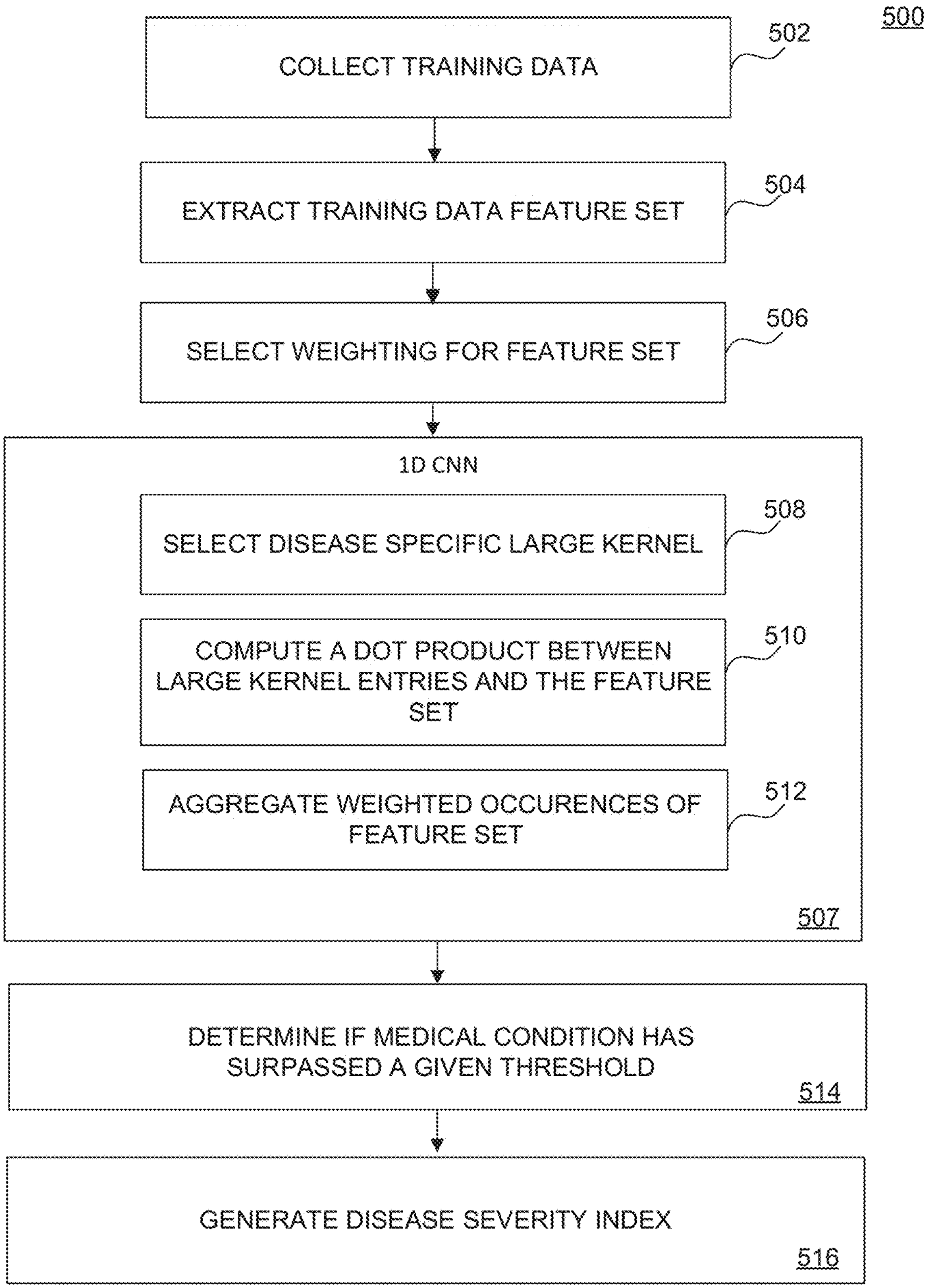
FIG. 5 is a flowchart illustrating a modeling process, according to some embodiments.

FIG. 5 is a flowchart illustrating a modeling process, according to some embodiments.

In 502, the machine learning system collects training data. The training data may be electronic health records (EHR) of a patient set. They may be intended for treatment, insurance claims, billing, or demand forecasting for treatment facilities. This may lead to focusing on specific categories of data (e.g., ICD codes, medical history) that would be of most use in predictive model building.

In 504, the machine learning system extracts a training data feature set during a data engineering stage. As earlier described in FIG. 2 descriptions, during a data engineering stage, the data is cleaned, processed, and different data sets are fused together. These processes may include how to treat null or missing values, establish standards for formatting columns and datatype selection, select a self-consistent time range among the data sets (e.g., verify the time ranges of all data sets and selecting a common time range useful for modeling), determining filtering criteria, and determining common joining keys. This may include EDA and several iterations.

Each observation within the final data set has a unique identifier for each subject (patient) member, a timestamp to signifying the first occurrence of an event, and an F-dimensional array of predictors $\{x_1, x_2, \ldots x_f\}$. The predictors from multiple event-related data are assembled in a quasi-static manner. Medical encounters are combined in a longitudinal (time-dependent) manner. This initial feature engineering may be performed based on domain knowledge and data exploration.

The feature engineering for the model may include medical encounter information to be chronologically ordered. When taken together, the sequential medical records represent the evolution of any given medical condition.

In 506, the machine learning system selects weighting of features within the feature set. For example, to optimize a value of longitudinal medical history records as a data source, it is critical to incorporate all available information for a given medical condition in a temporal fashion (e.g., the initial diagnosis, the frequency of occurrence and medical treatment, and how close the relevant diagnoses are to the decision point). As previously discussed, weighting may be assigned based on this temporal distribution, with newest occurrences being weighted the highest (reverse chronology). In this way, the feature engineering focused on creating features that preserve contextual information from longitudinal health records.

In 507, the machine learning system performs a one-dimensional convolutional of the weighted training data set using a large kernel. For example, in 508, the machine learning system selects a disease specific large kernel (filter). In 510, the machine learning system computes a dot product (detects occurrences of features over time) between large kernel entries and the feature set. In 512, the machine learning system aggregates weighted occurrences of the feature set.

In 514, the process identifies whether the medical condition has surpassed a given threshold. This is especially true for chronic conditions. The valuable temporal information from longitudinal health records can be partially preserved by creating, in 516, an index that combines the information from the longitudinal nature of the health record into a single index representing the medical condition severity. Before a decision on the severity of a given medical condition can be made, the temporal dependencies of encounter records must be considered. One non-limiting example approach to handling temporal dependencies is direct aggregation of encounter numbers in which temporal relations between different encounters are left out. One skilled in the art will appreciate that other approaches to handling temporal dependencies may be contemplated within the scope of the technology described herein.

Figure 6:
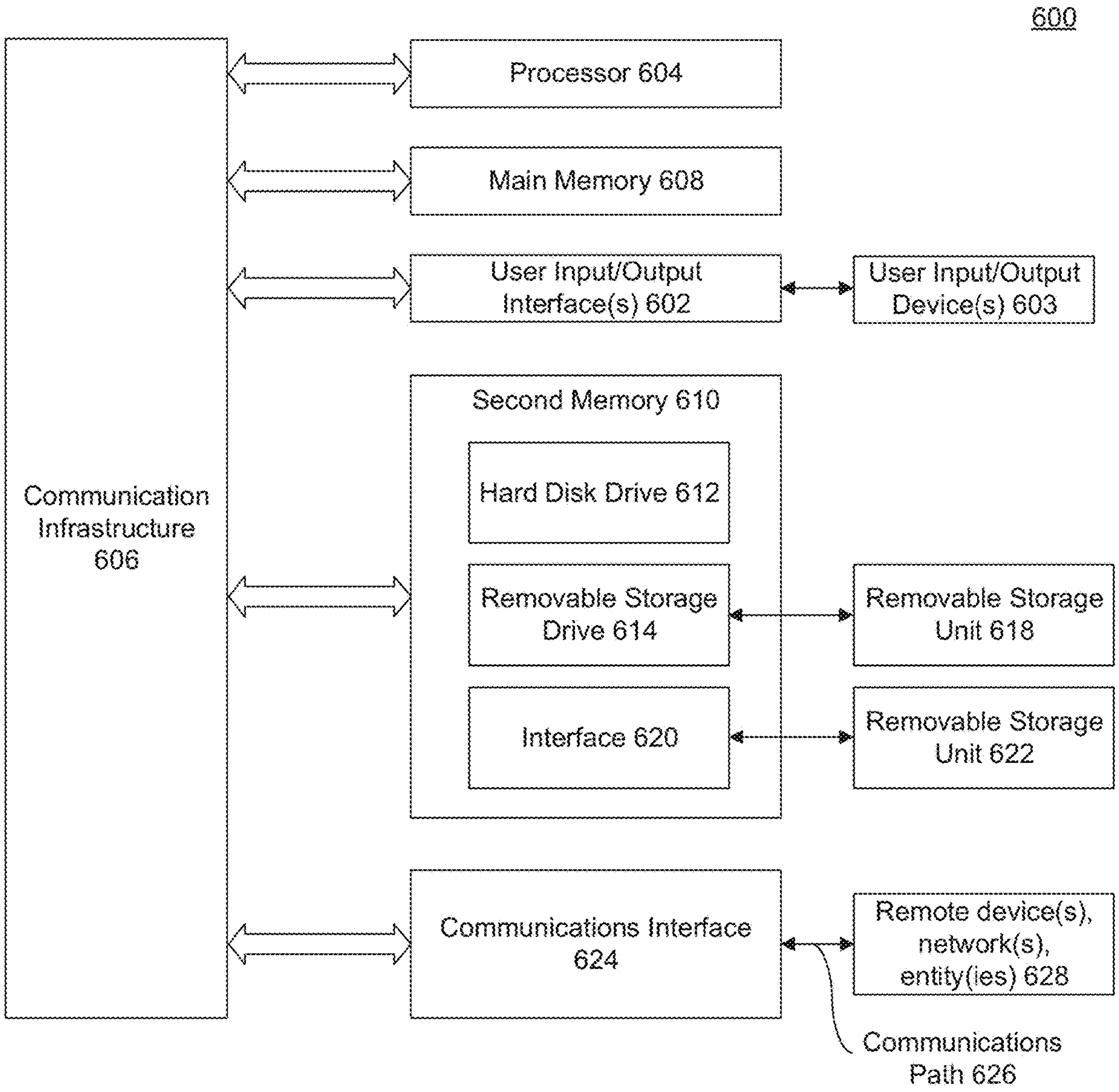
FIG. 6 is an example computer system useful for implementing various embodiments.

Various embodiments can be implemented, for example, using one or more computer systems, such as computer system 600 shown in FIG. 6. Computer system 600 can be used, for example, to implement method 500 of FIG. 5. For example, computer system 600 can determine a disease severity index. Computer system 600 can be any computer capable of performing the functions described herein.

Computer system 600 can be any well-known computer capable of performing the functions described herein.

Computer system 600 includes one or more processors (also called central processing units, or CPUs), such as a processor 604. Processor 604 is connected to a communication infrastructure or bus 606.

One or more processors 604 may each be a graphics processing unit (GPU). In an embodiment, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 600 also includes user input/output device(s) 603, such as monitors, keyboards, pointing devices, etc., that communicate with communication infrastructure or bus 606 through user input/output interface(s) 602.

Computer system 600 also includes a main or primary memory 608, such as random access memory (RAM). Main memory 608 may include one or more levels of cache. Main memory 608 has stored therein control logic (i.e., computer software) and/or data.

Computer system 600 may also include one or more secondary storage devices or memory 610. Secondary memory 610 may include, for example, a hard disk drive 612 and/or a removable storage device or drive 614. Removable storage drive 614 may be a floppy disk drive, a magnetic tape drive, a compact disk drive, an optical storage device, tape backup device, and/or any other storage device/drive.

Removable storage drive 614 may interact with a removable storage unit 618. Removable storage unit 618 includes a computer usable or readable storage device having stored thereon computer software (control logic) and/or data. Removable storage unit 618 may be a floppy disk, magnetic tape, compact disk, DVD, optical storage disk, and/any other computer data storage device. Removable storage drive 614 reads from and/or writes to removable storage unit 618 in a well-known manner.

According to an exemplary embodiment, secondary memory 610 may include other means, instrumentalities or other approaches for allowing computer programs and/or other instructions and/or data to be accessed by computer system 600. Such means, instrumentalities or other approaches may include, for example, a removable storage unit 622 and an interface 620. Examples of the removable storage unit 622 and the interface 620 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 600 may further include a communication or network interface 624. Communication interface 624 enables computer system 600 to communicate and interact with any combination of remote devices, remote networks, remote entities, etc. (individually and collectively referenced by reference number 628). For example, communication interface 624 may allow computer system 600 to communicate with remote devices 628 over communications path 626, which may be wired and/or wireless, and which may include any combination of LANs, WANs, the Internet, etc. Control logic and/or data may be transmitted to and from computer system 600 via communication path 626.

In an embodiment, a tangible, non-transitory apparatus or article of manufacture comprising a tangible, non-transitory computer useable or readable medium having control logic (software) stored thereon is also referred to herein as a computer program product or program storage device. This includes, but is not limited to, computer system 600, main memory 608, secondary memory 610, and removable storage units 618 and 622, as well as tangible articles of manufacture embodying any combination of the foregoing. Such control logic, when executed by one or more data processing devices (such as computer system 600), causes such data processing devices to operate as described herein.

Based on the teachings contained in this disclosure, it will be apparent to persons skilled in the relevant art(s) how to make and use embodiments of this disclosure using data processing devices, computer systems and/or computer architectures other than that shown in FIG. 6. In particular, embodiments can operate with software, hardware, and/or operating system implementations other than those described herein.

It is to be appreciated that the Detailed Description section, and not any other section, is intended to be used to interpret the claims. Other sections can set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments can perform functional blocks, steps, operations, methods, etc. using orderings different than those described herein.

References herein to "one embodiment," "an embodiment," "an example embodiment," or similar phrases, indicate that the embodiment described can include a particular feature, structure, or characteristic, but every embodiment can not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein. Additionally, some embodiments can be described using the expression "coupled" and "connected" along with their derivatives. These terms are not necessarily intended as synonyms for each other. For example, some embodiments can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary embodiments, but should be defined only in accordance with the following claims and their equivalents.

What is claimed is:

1. A computer implemented method, comprising:

collecting, by a machine learning system, training data sets;

extracting, by the machine learning system, a training data feature set from the training data sets;

weighting, by the machine learning system, one or more features in the training data feature set to generate a weighted training data feature set;

selecting, by the machine learning system, a large kernel comprising the training data feature set;

executing, by the machine learning system, a one-dimensional convolution of the weighted training data feature set, based on the large kernel, using a one-dimensional (1D) convolutional neural network (CNN) having a length representing a first time period and only a height representing a series of medical symptoms, to generate an aggregation of weighted occurrences, wherein the large kernel represents a filter covering a plurality of occurrences over a second time period that is convolved across the height of the 1D CNN, the second time period being smaller than the first time period; and generating, by the machine learning system, an index based on the aggregation of weighted occurrences;

wherein at least one of the collecting, extracting, weighting, selecting, applying and generating are performed by one or more computers.

2. The method of claim 1, wherein the executing the one-dimensional convolution further comprises processing a dot product between entries of the large kernel and the training data feature set to generate the weighted occurrences and aggregating the weighted occurrences.

3. The method of claim 1, wherein the large kernel comprises any of a disease specific filter, an injury specific filter or a medical condition specific filter.

4. The method of claim 3, wherein the generating the index further comprises identifying whether the aggregation of weighted occurrences surpasses a given threshold.

5. The method of claim 4, wherein the given threshold reflects a severity of any of a disease, an injury or a medical condition.

6. The method of claim 1, wherein the weighting of one or more features further comprises applying a temporal distribution.

7. The method of claim 6, wherein the temporal distribution assigns weighting based on a reverse chronology.

8. The method of claim 1, wherein the large kernel further comprises a gamma window function.

9. The method of claim 1, further comprising selecting a common time range of the training data sets.

10. The method of claim 1, wherein the training data feature set comprises a unique identifier for a patient, a timestamp to signifying a first occurrence of an event, and an F-dimensional array of predictors $\{x_1, x_2, \ldots x_f\}$.

11. The method of claim 1, wherein the training data set comprises a longitudinal, time-dependent, series of medical events.

12. A system, comprising:

a memory; and at least one processor coupled to the memory and configured to:

collect training data sets;

extract a training data feature set from the training data sets;

weight features in the training data feature set to generate a weighted training data feature set;

select a large kernel comprising the weighted training data feature set;

execute a one-dimensional convolution of the weighted training data feature set based on the large kernel, using a one-dimensional (1D) convolutional neural network (CNN) having a length representing a first time period and only a height representing a series of medical symptoms, to generate an aggregation of weighted occurrences, wherein the large kernel represents a filter covering a plurality of occurrences over a second time period that is convolved across the height of the 1D CNN, the second time period being smaller than the first time period; and generate an index based on the aggregation of weighted occurrences.

13. The system of claim 12, wherein to execute the one-dimensional convolution of the weighted training data feature set, the at least one processor is configured to execute the 1D CNN.

14. The system of claim 12, wherein to execute the one-dimensional convolution of the weighted training data feature set, the at least one processor is configured to process a dot product between entries of the large kernel and the training data feature set to generate the weighted occurrences and aggregate the weighted occurrences.

15. The system of claim 12, wherein the large kernel comprises any of a disease specific filter, an injury specific filter or a medical condition specific filter.

16. The system of claim 12, wherein to generate the index, the at least one processor is configured to identify whether the aggregation of weighted occurrences surpasses a given threshold.

17. The system of claim 16, wherein the given threshold reflects a relative severity of any of a disease, an injury or a medical condition.

18. The system of claim 12, wherein to weight the features, the at least one processor is further configured to apply a temporal distribution based on a reverse chronology.

19. A non-transitory computer-readable device having instructions stored thereon that, when executed by at least one computing device, cause the at least one computing device to perform operations comprising:

collecting training data sets;

extracting a training data feature set from the training data sets;

weighting features in the training data feature set to generate a weighted training data feature set;

selecting a large kernel comprising the weighted training data feature set;

executing a one-dimensional convolution of the weighted training data feature set based on the large kernel, using a one-dimensional (1D) convolutional neural network (CNN) having a length representing a first time period and only a height representing a series of medical symptoms, to generate an aggregation of weighted occurrences, wherein the large kernel represents a filter covering a plurality of occurrences over a second time period that is convolved across the height of the 1D CNN, the second time period being smaller than the first time period; and generating an index based on the aggregation of weighted occurrences.

* * * * *